United States Patent
Lorenzo et al.

(10) Patent No.: US 11,844,527 B2
(45) Date of Patent: *Dec. 19, 2023

(54) ENDOVASCULAR DETACHMENT SYSTEM WITH FLEXIBLE DISTAL END AND HEATER ACTIVATED DETACHMENT

(71) Applicant: DePuy Synthes Products, Inc., Raynham, MA (US)

(72) Inventors: Juan Lorenzo, Davie, FL (US); Robert Echarri, Miami, FL (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 269 days.

This patent is subject to a terminal disclaimer.

(21) Appl. No.: 17/348,274

(22) Filed: Jun. 15, 2021

(65) Prior Publication Data

US 2021/0307758 A1 Oct. 7, 2021

Related U.S. Application Data

(60) Continuation of application No. 16/257,149, filed on Jan. 25, 2019, now Pat. No. 11,051,823, which is a (Continued)

(51) Int. Cl.
*A61B 17/12* (2006.01)
*A61F 2/01* (2006.01)
*A61F 2/95* (2013.01)

(52) U.S. Cl.
CPC .... *A61B 17/1214* (2013.01); *A61B 17/12031* (2013.01); *A61B 17/1215* (2013.01); (Continued)

(58) Field of Classification Search
CPC .................. A61B 17/1214; A61B 17/12031
See application file for complete search history.

(56) References Cited

U.S. PATENT DOCUMENTS 6,102,932 A   8/2000   Kurz
6,280,457 B1  8/2001   Wallace et al.
(Continued)

FOREIGN PATENT DOCUMENTS

AU   2015227527 A1   4/2016
CN   102481436 A     5/2012
(Continued)

OTHER PUBLICATIONS

Notification of Reasons for Refusal issued in Japanese Patent Application No. 2017-107686 dated May 25, 2021, English translation only.

(Continued)

*Primary Examiner* — Phong Son H Dang
(74) *Attorney, Agent, or Firm* — TROUTMAN PEPPER HAMILTON SANDERS LLP

(57) ABSTRACT

An endovascular surgical tool may include a flexible, electrically-conductive delivery tube, a return conductor, a resistive heating element attached to the distal end of the delivery tube, and a therapeutic payload attached to a loop of the resistive heating element by a coil connecting member. The delivery tube may include at least one segment at its distal end which includes a plurality of transverse slots. Each slot of the plurality of slots includes an origin on the perimeter of the delivery tube, a terminus closer to a central axis of the delivery tube than the origin, and a depth between the origin and terminus. The origins of at least two slots of the plurality of slots may be located at different angular positions relative to the central axis. The return conductor may be electrically insulated from and positioned within the delivery tube.

15 Claims, 3 Drawing Sheets

Related U.S. Application Data division of application No. 15/170,204, filed on Jun. 1, 2016, now Pat. No. 10,285,710.

(52) U.S. Cl.
CPC . *A61B 17/12113* (2013.01); *A61B 2017/1205* (2013.01); *A61B 2017/12068* (2013.01); *A61F 2/01* (2013.01); *A61F 2/011* (2020.05); *A61F 2/95* (2013.01)

(56) References Cited

U.S. PATENT DOCUMENTS

| | | | |
|---|---|---|---|
| 6,391,037 B1 | 5/2002 | Greenhalgh | |
| 6,478,773 B1 | 11/2002 | Gandhi et al. | |
| 7,255,707 B2 | 8/2007 | Ramzipoor et al. | |
| 7,422,569 B2 | 9/2008 | Wilson et al. | |
| 7,582,101 B2 | 9/2009 | Jones et al. | |
| 7,942,894 B2 | 5/2011 | West | |
| 8,834,515 B2 | 9/2014 | Win et al. | |
| 8,940,011 B2 | 1/2015 | Teoh et al. | |
| 8,974,488 B2 | 3/2015 | Tan et al. | |
| 8,998,926 B2 | 4/2015 | Pomeranz | |
| 9,119,948 B2 | 9/2015 | Lee et al. | |
| 9,149,278 B2 | 10/2015 | Slazas et al. | |
| 9,155,540 B2 | 10/2015 | Lorenzo | |
| 9,232,992 B2 | 1/2016 | Heidner | |
| 9,314,250 B2 | 4/2016 | Chen et al. | |
| 9,451,964 B2 | 9/2016 | Guo et al. | |
| 9,480,479 B2 | 11/2016 | Chen et al. | |
| 9,504,475 B2 | 11/2016 | Chen et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,782,178 B2 | 10/2017 | Lorenzo | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,814,465 B2 | 11/2017 | Win et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,855,050 B2 | 1/2018 | Lorenzo et al. | |
| 9,918,718 B2 | 3/2018 | Lorenzo | |
| 9,980,731 B2 | 5/2018 | Lorenzo | |
| 10,517,604 B2 | 12/2019 | Bowman et al. | |
| 2004/0034363 A1 | 2/2004 | Wilson et al. | |
| 2005/0149108 A1 | 7/2005 | Cox | |
| 2006/0064151 A1 | 3/2006 | Guterman | |
| 2006/0135986 A1 | 6/2006 | Wallace | |
| 2008/0281350 A1 | 11/2008 | Sepetka | |
| 2008/0306504 A1 | 12/2008 | Win et al. | |
| 2009/0163780 A1* | 6/2009 | Tieu | A61F 2/966 623/1.11 |
| 2009/0177261 A1 | 7/2009 | Teoh et al. | |
| 2010/0160944 A1* | 6/2010 | Teoh | A61B 17/12154 606/191 |
| 2010/0324649 A1 | 12/2010 | Mattsson | |
| 2011/0301686 A1* | 12/2011 | Bowman | A61M 25/0021 623/1.11 |
| 2012/0209310 A1 | 8/2012 | Chen et al. | |
| 2012/0283768 A1 | 11/2012 | Cox et al. | |
| 2013/0138136 A1 | 5/2013 | Beckham et al. | |
| 2013/0261656 A1 | 10/2013 | Lorenzo | |
| 2013/0261658 A1* | 10/2013 | Lorenzo | A61B 17/1214 606/200 |
| 2013/0261659 A1* | 10/2013 | Lorenzo | A61B 17/12031 606/200 |
| 2013/0261713 A1* | 10/2013 | Lorenzo | A61B 17/1214 607/113 |
| 2014/0088585 A1 | 3/2014 | Hill et al. | |
| 2014/0135812 A1 | 5/2014 | Divino et al. | |
| 2014/0200607 A1 | 7/2014 | Sepetka et al. | |
| 2014/0277078 A1* | 9/2014 | Slazas | A61B 17/1214 606/200 |
| 2014/0277084 A1 | 9/2014 | Mirigian | |
| 2014/0277092 A1 | 9/2014 | Teoh et al. | |
| 2014/0277093 A1 | 9/2014 | Guo et al. | |
| 2014/0277094 A1* | 9/2014 | Chen | A61B 17/12022 606/200 |
| 2015/0057700 A1* | 2/2015 | Chen | A61B 17/1214 606/200 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |

(56) References Cited

U.S. PATENT DOCUMENTS

| | | |
|---|---|---|
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | |
|---|---|---|
| CN | 103356261 A | 10/2013 |
| CN | 105434004 A | 3/2016 |
| JP | 2010-527702 A | 8/2010 |
| JP | 2014-176667 A | 9/2014 |
| JP | 2016-59814 A | 4/2016 |

OTHER PUBLICATIONS

Partial European Search Report dated Feb. 12, 2018 for European Patent Application No. 17173653.1.

Search Report issued in corresponding Chinese Patent Application No. 201710403995.X dated Dec. 2, 2020, English translation only.

* cited by examiner

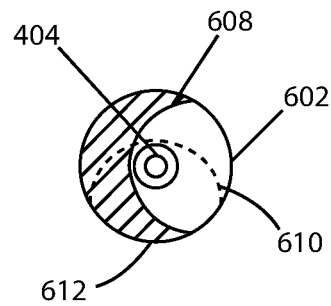
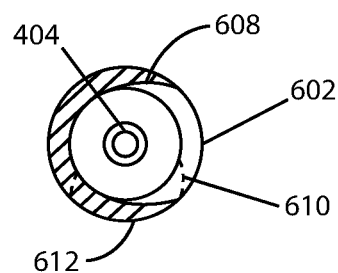
FIG. 6A    FIG. 6B
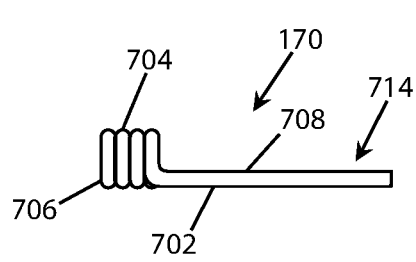
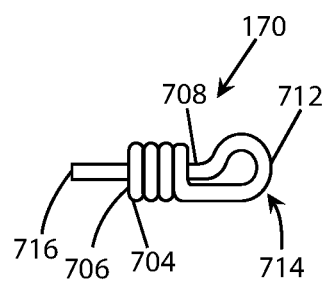
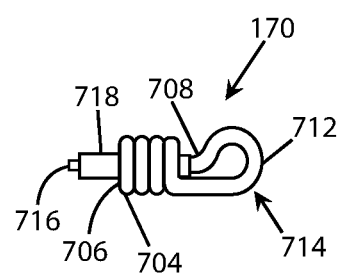
FIG. 7A    FIG. 7B    FIG. 7C
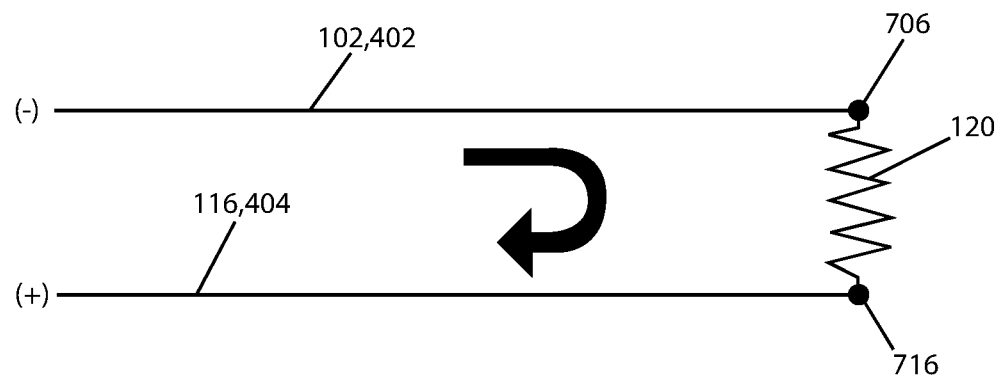
FIG. 8

ENDOVASCULAR DETACHMENT SYSTEM WITH FLEXIBLE DISTAL END AND HEATER ACTIVATED DETACHMENT

CROSS-REFERENCE TO RELATED APPLICATIONS

This application is a continuation application of U.S. patent application Ser. No. 16/257,149 filed Jan. 25, 2019, which is a divisional application of U.S. patent application Ser. No. 15/170,204 filed Jun. 1, 2016, now U.S. Pat. No. 10,285,710. The contents of which are incorporated herein by reference in their entirety as if set forth verbatim

FIELD

The present disclosure relates generally to surgical tools for treating defects in the vasculature by placing interventional treatment devices within the vasculature. More particularly, it relates to devices for releasing therapeutic treatments from the distal end of a catheter.

BACKGROUND

Endovascular therapies such as embolic coils, stents, plugs, and the like are typically placed within the vasculature by use of a catheter. For example, embolic coils may be placed within a ruptured aneurysm to form an embolus within the aneurysm and occlude the flow of blood into aneurysm. Such endovascular therapies are pushed through the lumen of a catheter to the treatment location and deployed into the area to be treated.

Inserting a guiding catheter or delivery catheter system to a desired treatment site is the first step for modern forms of endovascular treatment, and one of the most important steps for treatment of defects in the neurovasculature. The size of the vasculature, especially around the treatment site, frequently makes accurate placement and reliable detachment of the therapy difficult. It is desirable to maximize both the flexibility of the distal end of the placement tool and the reliability of detaching the therapy.

SUMMARY

In one example, an endovascular surgical tool includes a flexible, electrically-conductive corewire, a return conductor, a resistive heating element attached to the distal end of the corewire, and a therapeutic payload attached to a loop of the resistive heating element by a coil connecting member. The corewire may include at least one segment at its distal end which transitions from a substantially uniform proximal cross-section to a smaller distal cross-section. The return conductor is electrically insulated from and bonded to the corewire. The resistive heating element may include a first terminal electrically connected to the corewire, a second terminal electrically connected to the return conductor, a helical coil, and a loop. The helical coil and the loop are electrically in series between the first terminal and the second terminal. The coil connecting member may have a release temperature lower than the melting temperature of the loop.

In a further example, the resistive heating element further may include a single length of electrically conductive material forming the first terminal, the second terminal, the helical coil, and the loop. The helical coil may be formed along an axis substantially collinear with the central axis of the corewire and may include a first coil end and a second coil end, where the first coil end abuts either the first terminal or the second terminal and where the second coil end abuts the loop. The loop may be positioned distally relative to the helical coil and may include a first loop end and a second loop end, where the first loop end abuts the second coil end and the second loop end is formed through an inner diameter of the helical coil and abuts whichever of the first terminal and the second terminal does not abut the first coil end. The resistive heating element further may also include an electrically insulating sleeve encapsulating portions of the second loop end and second terminal which are in proximity to the first terminal and the inner diameter of the helical coil. The resistive heating element may also include a protective sleeve encapsulating at least a portion of the outer diameter of the helical coil.

In another example, the endovascular surgical tool may include an embolic coil as the therapeutic payload. The embolic coil may include a coil helix with a proximal end and a distal end, a proximal coil junction abutting the proximal end of the coil helix, a distal bead abutting the distal end of the coil helix, and at least one suture filament positioned within the coil helix and attached to the proximal coil junction and the distal bead.

In another example, the coil connecting member may include a temperature sensitive polymer. In another example, the proximal end and distal end of the corewire include different materials.

In another example, an endovascular surgical tool may include a flexible, electrically-conductive delivery tube, a return conductor, a resistive heating element attached to the distal end of the delivery tube, and a therapeutic payload attached to a loop of the resistive heating element by a coil connecting member. The delivery tube may include at least one segment at its distal end which includes a plurality of transverse slots. Each slot of the plurality of slots includes an origin on the perimeter of the delivery tube, a terminus closer to a central axis of the delivery tube than the origin, and a depth between the origin and terminus. The origins of at least two slots of the plurality of slots may be located at different angular positions relative to the central axis. The return conductor may be electrically insulated from and positioned within the delivery tube. The resistive heating element may include a first terminal electrically connected to the distal end of the delivery tube, a second terminal electrically connected to the distal end of the return conductor, a helical coil, and a loop. The helical coil and the loop are electrically in series between the first terminal and the second terminal. The coil connecting member may have a release temperature lower than the melting temperature of the loop. In another example, the proximal end and distal end of the delivery tube may include different materials.

BRIEF DESCRIPTION OF THE DRAWINGS

FIG. 6A is a cross-section of a thick-walled slotted delivery tube illustrating one example of slots cut with a rotational cutting tool.

FIG. 6B is a cross-section of a thin-walled slotted delivery tube illustrating another example of slots cut with a rotational cutting tool.

FIG. 7A is an illustration of a heater during an initial stage of its manufacture, in accordance with the present disclosure.

FIG. 7B is an illustration of the heater during an intermediate stage of its manufacture, in accordance with the present disclosure.

FIG. 7C is an illustration of the heater during the final stage of its manufacture, in accordance with the present disclosure.

FIG. 8 is a circuit diagram illustrating the electrical operation of the heater.

DETAILED DESCRIPTION

Figure 1:
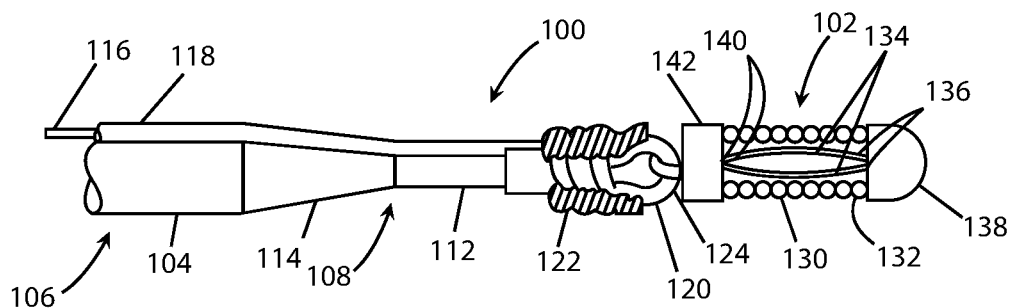
FIG. 1 is an illustration of one example of an endovascular surgical tool including a tapered corewire and illustrating the tool's functional components and their relationship to each other, in accordance with the present disclosure.

The surgical device includes a flexible delivery member, an insulated return conductor, and a heating element electrically connected to both and positioned at the end of the delivery tube. Referring now to the Figures, in which like reference numerals represent like parts, various examples of the computing devices and methods will be disclosed in detail.

Delivery Member

FIG. 1 is an illustration of one example of an endovascular detachment system 100. The therapy 102 to be delivered is pushed into position through the catheter by a flexible delivery tube (not shown) or a flexible corewire 104. In FIG. 1, the therapy 102 is an embolic coil, although other therapies may be delivered by the same or similar means. The delivery tube and/or corewire 104 may typically have cylindrical cross-sections. The delivery tube and/or corewire may be manufactured from any biocompatible electrically conductive material. Either the delivery tube or the corewire 104 may be of a single piece construction or may have a proximal end 106 consisting of one material (such as Stainless Steel) and a distal end 108 connected to the proximal end 106 and made of a different material (such as Nitinol). The delivery member is stiffer over its proximal end 106 and flexible towards the distal end 108 of the tube. The distal end of the flexible delivery member may incorporate special features to enhance its flexibility. In one example, the distal end 108 of a corewire 104 may be tapered to reduce its stiffness and increase its flexibility. In another example, the distal end of the corewire 104 may have multiple tapers. In another example, the distal end of a delivery tube may include a series of partial transverse slots 408 or slots, perpendicular to the axis of the delivery tube to reduce its stiffness and increase its flexibility.

Corewire with Tapered Distal End

In this example, shown in FIG. 1, the flexibility of the distal end of the corewire 104 is achieved by reducing the cross section of at least part of the distal end 108. In some examples, the corewire 104 may taper 114 from one cross section to another cross section 112. In other examples, the transition between cross sections may be abrupt or stepped, rather than tapered. For convenience, and without limitation, the remainder of this disclosure will refer to tapered transitions. The length and number of tapers will determine the flexibility of the distal section.

An insulated return conductor 116 is attached to the outer surface of the corewire 104. In some examples, the insulation 118 of the return conductor 116 may be bonded to the corewire 104. Together, the corewire 104 and the return conductor 116 supply electrical power to an electrical heater 120 connected at the distal end 108 of the corewire 104. The heater 120 allows detachment of the therapy 102.

Figure 2:
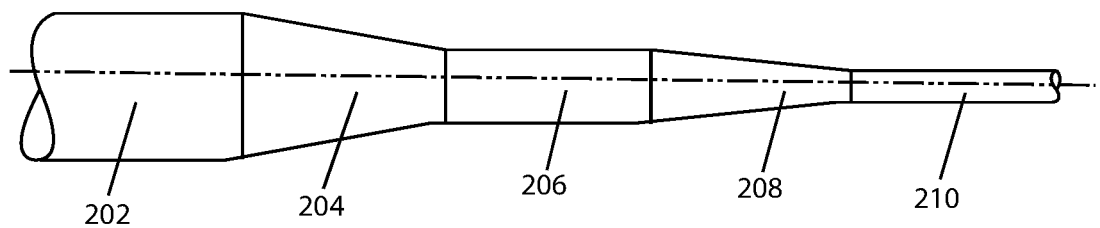
FIG. 2 is an illustration of another example of a tapered corewire including several tapered sections, in accordance with the present disclosure.

Several examples may be employed to control the flexibility of the distal end of the corewire 104. In one example the corewire 104 may taper 114 to a reduced cross-section 112 and then continue that reduced cross-section for some length before the heater is attached. In another example, the corewire 104 may taper to a reduced cross-section with the heater attached directly at the end of the taper. In another example, illustrated in FIG. 2, the corewire 202 may have two or more tapers 204, 208 resulting in progressively smaller cross sections 206, 210 and correspondingly increasing flexibility.

Figure 3:
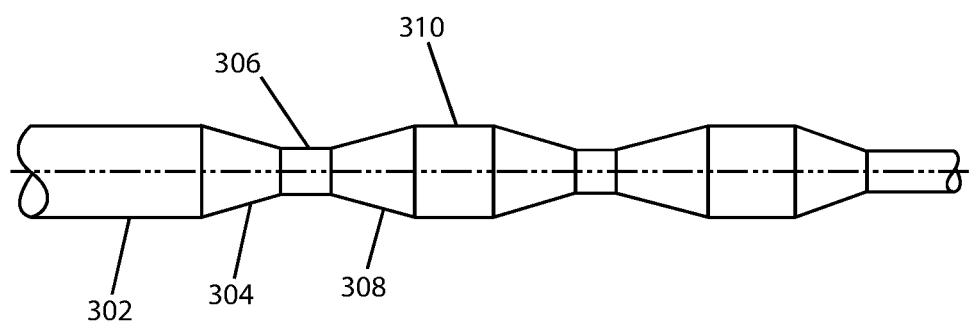
FIG. 3 is an illustration of another example of a tapered corewire including alternating tapered sections, in accordance with the present disclosure.

In another example, illustrated in FIG. 3, the corewire 302 may have one or more flexible sections interspersed between less flexible sections. For example, the cross section of the corewire 302 may taper down 304 to a reduced cross section 306 and then taper back up 308 to the larger cross section 310, producing a discreet flexible section which functionally resembles a joint. This technique may be repeated to produce a distal end of the corewire with segments that behave as if they were articulated.

Delivery Tube with Slotted Distal End

Figure 4:
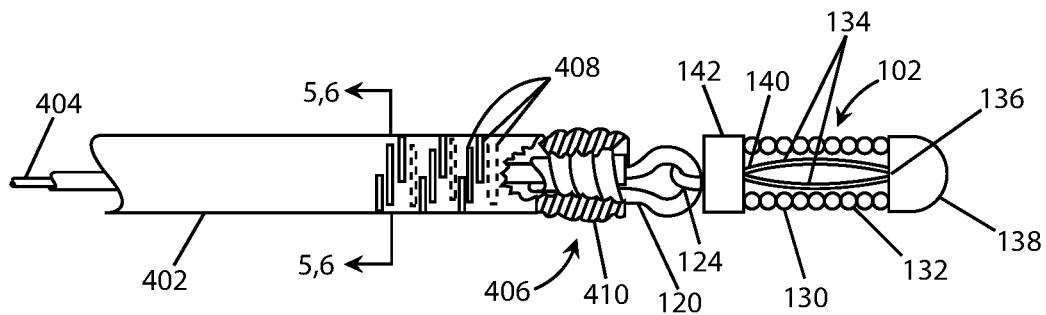
FIG. 4 is an illustration of one example of an endovascular surgical tool including a slotted delivery tube and illustrating the functional components and their relationship to each other, in accordance with the present disclosure.

In this example, illustrated in FIG. 4, the delivery member is a conductive delivery tube 402. A separate insulated return conductor 404 passes inside the lumen of the delivery tube 402.

In this example, the flexibility of the distal end 406 of the delivery tube is achieved by adding transverse cuts or slots 408 to the wall of the delivery tube 402 in an interrupted configuration. In order to maintain electrical conductivity, no single slot 408 completely perforates the outer perimeter of the delivery tube 402.

Figure 5A:
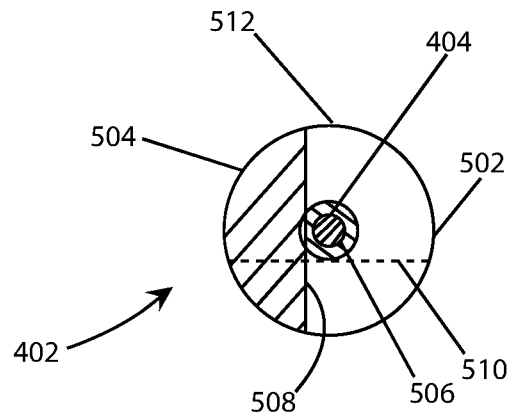
FIG. 5A is a cross-section of a thick-walled slotted delivery tube illustrating one example of slots cut with a straight cutting tool.
Figure 5B:
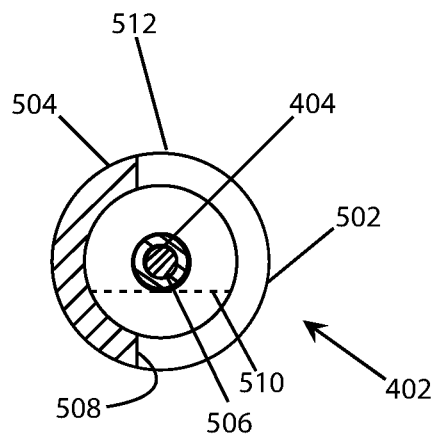
FIG. 5B is a cross-section of a thin-walled slotted delivery tube illustrating another example of slots cut with a straight cutting tool.

The cuts are placed in an interrupted configuration to retain the integrity of the flexible distal end 406. As illustrated in FIGS. 5A and 5B, each slot 408 originates at an origin point 502 on the circumference 504 of the delivery tube 402 and progresses inward toward the axis 506 of the delivery tube 402. In some examples, the slot 408 may progress past the central axis 506 of the delivery tube. The slots may be planar or curvilinear. Planar cuts 508, 510 may be perpendicular to the central axis of the delivery tube or made at an acute or obtuse angle to the central axis. Planar cuts may be made, for example, by a band saw, a laser, or a slot cutter traversing perpendicularly to the axis 506 of the delivery tube 402. Other techniques may also be used, as will be understood by those skilled in the art.

The radial position of the origin points 502 may be different between different individual cuts. For example, a first cut 508 may originate 502 at a radial position of 0°, followed by an additional cut 510 originating 512 at a radial position of 90°. Additional cuts may follow originating at 180°, 270°, etc., forming a spiral formation of cuts. Other radial spacings between slots may also be used.

FIGS. 6A and 6B illustrate curvilinear slots 608, 610 made in thick-walled and thin-walled delivery tubes 402, respectively. Curvilinear cuts 608, 610 may be perpendicular to the central axis 506 of the delivery tube 402 or made at an acute or obtuse angle relative to the axis 506 of the delivery tube 402. Curvilinear cuts may be made, for example using a rotating cutting wheel or slot cutter plunging into the delivery tube 402 from the origin 602, 612 of the slot toward the axis 506 of the delivery tube 402. Other techniques may also be used, as will be understood by those skilled in the art.

The radial position of the origin points may be different between different individual cuts. For example, a first cut 608 may originate 602 at a radial position of 0°, followed by an additional cut 610 originating 612 at a radial positions of 90°. Additional cuts may follow originating at 180°, 270°, etc., forming a spiral formation of cuts. Other radial spacings between slots may also be used.

Other combinations of radial origin positions may be employed to achieve particular flexibility profiles for particular applications, as will be understood by those skilled in the art. For example, slots 408 may alternate only on opposite sides of the delivery tube 402 (e.g. 0° and 180°) which enhances flexibility only in one plane relative to the axis 506 of the delivery tube 402.

The number and spacing between slots 408 along the axis of the delivery tube 402 also affect the stiffness of the tube. For example, slots 408 may be made in close proximity to each other to maximize the flexibility of the cut segment. The spacing of the slots 408 may be consistent or variable to achieve different effects. In one example, the spacing of slots 408 may decrease linearly from a proximal location to the distal end 406. This results in a gradually decreasing stiffness (increasing flexibility) progressing along the delivery tube axis toward the distal end. In another example, the slots may alternate between tight spacing and wider spacing, producing distinct regions of greater and lesser flexibility, respectively.

Detachment Mechanism

A heater 120 (electric resistive element) is formed out of a conductive wire 702 in several steps, illustrated in FIGS. 7A-7C. First, in FIG. 7A, the wire 702 is formed into a helically wound coil 704 having a flush-cut proximal end 706 which serves as a first terminal and a straight section of wire 708 at the distal end 714. In FIG. 7B the straight section 708 is bent, forming a loop 712 at the distal end 714 of the heater, with the remaining wire 716 threaded back through the center of the coil 704. In FIG. 7C an insulation sleeve 718 is placed over the remaining wire 716 to prevent electrical contact (a short circuit) between the straight section 708 of wire end the inner diameter of the coil 704. In some examples, the insulation sleeve 718 may also mechanically connect the heating element to the corewire 104 or delivery tube 402. The remaining wire 716 is then serves as a second terminal. Thus, in its final form, the heater 120 has a first terminal end 706, a helical coil 704, a loop 712, and a second terminal end 716, all electrically in series.

The first terminal 706 and second terminal 716 of the heater are electrically connected to the corewire/delivery tube 104, 402 and the return conductor 116, 404 by soldering, crimping, conductive epoxy, or other conductive means, as will be understood by those skilled in the art. In some examples, the first terminal 706 of the heater may be connected to the corewire/delivery tube 104, 402 and the second terminal 716 may be connected to the return conductor 116, 404. In other examples, the first terminal 706 of the heater may be connected to the return conductor 116, 404 and the second terminal 716 may be connected to the corewire/delivery tube 104, 402. In either example, electrical current can now flow through the path formed by the corewire/delivery tube 104, 402, the heater 120, and the return conductor 116, 404. The heater 120 is secured to the corewire/delivery 104, 402 tube by a heat shrinkable insulation/coupling sleeve 122, 410 placed over the joint.

The therapy 102 to be delivered is attached to the loop 712 of the heater 120 by a coil connecting member 124. The connecting member 124 is thermally sensitive and releases the therapy when the heater 120 heats it to a particular temperature. In some examples, the connecting member 124 has a melting point lower than the wire of the heater 120. In these examples, the heater 120 melts the connecting member 124, releasing the therapy 102. In some examples, for example, the connecting member may be made from a polymer with a relatively low melting temperature. Other temperature-sensitive materials may include shape-memory alloys, bimetallic structures, etc., which change shape when heated to release the therapy.

Embolic Coil

In one example, the therapy 102 may be an embolic component 130 formed in the shape of a coil 132. The coil 132 contains a suture filament 134 (or series of filaments) through its center. The distal end(s) 136 of the suture(s) 134 are attached to the distal end of the coil 132, forming a distal bead 138. The proximal end(s) 140 of the suture(s) 134 are secured to the coil at the coil proximal junction 142. The purpose of the suture(s) 134 is to provide stretch resistance to the coil 132. A coil connecting member 124, independent from the stretch-resistance suture(s) 134, is threaded through the loop 712 formed at the distal end 714 of the heating element 120 and both ends of the coil connecting member 124 are secured at the coil proximal junction 142. The embolic component 130 may thus be deployed by passing electrical current though the heater 120. The heat causes the coil connecting member 124 to release the embolic component 130, for example by melting.

Other therapies may also be deployed via the detachment system described in this disclosure. Examples include, without limitation: plugs, filters, vascular occlusion devices, stents and aneurysm intra-saccular devices.

To facilitate an understanding of the principals and features of the disclosed technology, illustrative examples are explained above. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

It must also be noted that, as used in the specification and the appended claims, the singular forms "a" "an" and "the" include plural referents unless the context clearly dictates otherwise.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An endovascular surgical tool comprising:
   a flexible, electrically-conductive delivery tube having a central axis, a proximal end, and a distal end, where at least one segment of the distal end further comprises a plurality of transverse slots; and
   a resistive heating element attached to the distal end of the delivery tube, the resistive heating element comprising:
   a first terminal electrically connected to the distal end of the delivery tube;
   a second terminal electrically connected to the distal end of a return conductor;
   a helical coil; and
   a loop connected electrically with the helical coil.

2. The endovascular surgical tool of claim 1, wherein the resistive heating element further comprises a single length of electrically conductive material forming the first terminal, the second terminal, the helical coil, and the loop, and wherein:
   the helical coil is formed along an axis collinear with the central axis of the delivery tube and comprises a first coil end and a second coil end, wherein the first coil end abuts one of the first terminal and the second terminal and wherein the second coil end abuts the loop.

3. The endovascular surgical tool of claim 2, wherein the loop is positioned distally relative to the helical coil and comprises a first loop end and a second loop end.

4. The endovascular surgical tool of claim 3, wherein the first loop end abuts the second coil end and the second loop end is formed through an inner diameter of the helical coil and abuts whichever of the first terminal and the second terminal does not abut the first coil end.

5. The endovascular surgical tool of claim 2, wherein the resistive heating element further comprises an electrically insulating sleeve encapsulating portions of the second loop end and second terminal in proximity to the first terminal and the inner diameter of the helical coil.

6. The endovascular surgical tool of claim 2, wherein the resistive heating element further comprises a protective sleeve encapsulating at least a portion of an outer diameter of the helical coil.

7. The endovascular surgical tool of claim 1, wherein the helical coil and the loop are electrically in series between the first terminal and the second terminal.

8. The endovascular surgical tool of claim 1, wherein the coil connecting member comprises a temperature sensitive polymer.

9. The endovascular surgical tool of claim 1, wherein the proximal end and distal end of the corewire comprise different materials.

10. The endovascular surgical tool of claim 1, further comprising a therapeutic payload attached to the loop of the resistive heating element by a coil connecting member.

11. The endovascular surgical tool of claim 10, wherein the coil connecting member has a release temperature lower than a loop melting temperature of the loop.

12. The endovascular surgical tool of claim 10, wherein the therapeutic payload is an embolic coil comprising:
   a coil helix comprising a proximal end and a distal end;
   a proximal coil junction abutting the proximal end of the coil helix; and
   a distal bead abutting the distal end of the coil helix.

13. The endovascular surgical tool of claim 12, the embolic coil further comprising at least one suture filament positioned within the coil helix and attached to the proximal coil junction and the distal bead.

14. The endovascular surgical tool of claim 1, wherein each slot of the plurality of transverse slots comprise an origin on a perimeter of the delivery tube, a terminus closer to the axis of the delivery tube than the origin, and a depth comprising the distance between the origin and terminus.

15. The endovascular surgical tool of claim 14, wherein the origins of at least two slots of the plurality of slots are located at different angular positions relative to the central axis.

* * * * *